United States Patent
Sato et al.

(10) Patent No.: US 8,541,700 B2
(45) Date of Patent: Sep. 24, 2013

(54) WEIGHT SCALE

(75) Inventors: Tetsuya Sato, Nishinomiya (JP); Feilang Tseng, Kyoto (JP); Tadashi Koike, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 956 days.

(21) Appl. No.: 12/452,022

(22) PCT Filed: Jun. 3, 2008

(86) PCT No.: PCT/JP2008/060188
§ 371 (c)(1),
(2), (4) Date: Dec. 11, 2009

(87) PCT Pub. No.: WO2008/152941
PCT Pub. Date: Dec. 18, 2008

(65) Prior Publication Data
US 2010/0130831 A1    May 27, 2010

(30) Foreign Application Priority Data
Jun. 11, 2007  (JP) .................. 2007-154053

(51) Int. Cl.
*G01G 19/40*    (2006.01)
*G01G 19/44*    (2006.01)

(52) U.S. Cl.
USPC ...... 177/25.19; 177/5; 177/25.11; 177/25.13; 177/25.16; 702/173

(58) Field of Classification Search
USPC .................. 177/25.12, 25.19; 702/173
See application file for complete search history.

(56) References Cited

U.S. PATENT DOCUMENTS

| | | | | |
|---|---|---|---|---|
| 4,301,879 A * | 11/1981 | Dubow | | 177/5 |
| 4,629,015 A * | 12/1986 | Fried et al. | | 177/25.19 |
| 5,839,901 A * | 11/1998 | Karkanen | | 434/127 |
| 6,354,996 B1 * | 3/2002 | Drinan et al. | | 600/300 |
| 6,516,221 B1 * | 2/2003 | Hirouchi et al. | | 600/547 |
| 6,617,530 B1 * | 9/2003 | Lin | | 177/25.16 |
| 6,679,854 B2 * | 1/2004 | Honda et al. | | 600/587 |
| 6,734,856 B2 * | 5/2004 | Ishikawa et al. | | 345/440 |

(Continued)

FOREIGN PATENT DOCUMENTS

| | | |
|---|---|---|
| JP | A-62-188913 | 8/1987 |
| JP | A-64-083108 | 3/1989 |

(Continued)

OTHER PUBLICATIONS

Apr. 3, 2012 Notice of Reason for Rejection issued in Japanese Patent Application No. 2007-154053 (with partial translation).

(Continued)

*Primary Examiner* — Leonard Chang
*Assistant Examiner* — Natalie Huls
(74) *Attorney, Agent, or Firm* — Oliff & Berridge, PLC

(57) ABSTRACT

A weight scale includes weight measurement means, storage means for storing a weight measurement value along with a measurement day and time, determination means for determining whether a fluctuation range of the weight measurement value in the same day is within a predetermined reference range, and display means for displaying a percentage of days determined that the daily weight fluctuation is within the reference range. In this manner, a trend in weight change can be grasped even with the measurement of a relatively short period.

7 Claims, 13 Drawing Sheets

(56) References Cited

U.S. PATENT DOCUMENTS

| | | | |
|---|---|---|---|
| 6,963,035 B2* | 11/2005 | Honda et al. | 177/25.19 |
| 7,459,644 B2* | 12/2008 | Kenmochi | 177/1 |
| 7,547,851 B1* | 6/2009 | Wong | 177/25.13 |
| 7,917,329 B2* | 3/2011 | Hamamoto | 702/173 |
| 7,979,116 B2* | 7/2011 | Tseng et al. | 600/547 |
| 7,994,439 B2* | 8/2011 | Daniels et al. | 177/25.13 |
| 8,200,453 B2* | 6/2012 | Gage et al. | 702/173 |
| 2002/0112898 A1* | 8/2002 | Honda et al. | 177/245 |
| 2004/0162702 A1* | 8/2004 | Pandipati et al. | 702/173 |
| 2004/0238228 A1* | 12/2004 | Montague et al. | 177/25.13 |
| 2005/0209528 A1* | 9/2005 | Sato et al. | 600/547 |
| 2008/0103375 A1* | 5/2008 | Kiani | 600/323 |
| 2009/0089672 A1* | 4/2009 | Tseng et al. | 715/700 |
| 2009/0118589 A1* | 5/2009 | Ueshima et al. | 600/300 |
| 2009/0131812 A1* | 5/2009 | Sato et al. | 600/547 |
| 2009/0264790 A1* | 10/2009 | Ashida et al. | 600/547 |
| 2010/0106045 A1* | 4/2010 | Sato et al. | 600/547 |
| 2010/0312074 A1* | 12/2010 | Sato et al. | 600/300 |
| 2010/0331629 A1* | 12/2010 | Sato et al. | 600/300 |
| 2011/0106553 A1* | 5/2011 | Sato et al. | 705/2 |
| 2011/0295145 A1* | 12/2011 | Sato | 600/547 |
| 2011/0301916 A1* | 12/2011 | Oshima et al. | 702/173 |
| 2012/0302843 A1* | 11/2012 | Otsubo et al. | 600/301 |
| 2012/0330683 A1* | 12/2012 | Ledwidge et al. | 705/3 |
| 2013/0131463 A1* | 5/2013 | Date et al. | 600/301 |

FOREIGN PATENT DOCUMENTS

| | | |
|---|---|---|
| JP | A-6-167382 | 6/1994 |
| JP | A-2001-022837 | 1/2001 |
| JP | A-2002-112976 | 4/2002 |
| JP | A-2002-159450 | 6/2002 |
| JP | A-2003-265427 | 9/2003 |
| JP | A-2003-315142 | 11/2003 |
| JP | A-2005-218582 | 8/2005 |
| JP | B2-3722678 | 11/2005 |
| JP | B2-3818488 | 9/2006 |
| WO | WO 2006/070827 A1 | 7/2006 |

OTHER PUBLICATIONS

Apr. 3, 2012 Japanese Office Action issued in Japanese Patent Application No. 2009-242622 (with translation).

Jul. 31, 2012 Office Action issued in Japanese Patent Application No. 2007-154053 with translation.

International Search Report issued in International Application No. PCT/JP2008/060188; Mailed on Aug. 12, 2008.

* cited by examiner

[1] Display after morning measurement

[2] Display after night measurement

[3] Determination display
of one week (A) Time of morning measurement

WEIGHT SCALE

TECHNICAL FIELD

The present invention relates to a weight scale, and in particular, to a display method in the weight scale.

BACKGROUND ART

Various methods are conventionally proposed for a display method of a measurement result by a weight scale or a body composition meter. For instance, devises to enable a user to easily understand a history of the measurement result when displaying the past weight measurement results in time-series are proposed (Patent Documents 1, 2). There is also proposed a technique for maintaining a motivation with respect to diet by setting a health management goal and displaying the history of the weight along with a target achievement (score) (Patent Document 3).

Taking into consideration that a weight of a person fluctuates in a day (daily fluctuation), a technique of creating reference data, which becomes a target of comparison, from the past data measured at the same time as the measurement time of the weight, and displaying the comparison result with the reference data is disclosed in Patent Document 4. In Patent Document 4, the daily fluctuation of the measurement day is compared with the daily fluctuation of the past, and whether the weight demonstrates an upward trend or a downward trend is displayed.

Patent Document 1: Japanese Patent Publication No. 3722678
Patent Document 2: Japanese Patent Publication No. 3818488
Patent Document 3: Japanese Unexamined Patent Publication No. 2003-265427
Patent Document 4: Japanese Unexamined Patent Publication No. 2005-218582

DISCLOSURE OF THE INVENTION

Problems to be Solved by the Invention

In the weight scale described in Patent Documents 1 to 3, a weight fluctuation in a day is not taken into consideration, and thus a trend in weight change is difficult to grasp due to a fluctuation caused by variation of weight from a difference in measurement time. In order to grasp the correct trend, the measurement needs to be performed continuously for a period of a certain extent, but a motivation is difficult to maintain without being able to grasp the trend in change when measurement is performed continuously for a long period of time.

The weight scale described in Patent Document 4 takes into consideration the daily fluctuation, but the measurement needs to be performed continuously for a period of a certain extent to create reference data. Furthermore, although the daily fluctuation of the past and the daily fluctuation of the current day are compared to determine whether the weight demonstrates an upward trend or a downward trend, the current trend in change cannot be determined simply from a magnitude comparison with the reference value if the measurement data of the past already demonstrates an upward trend or a downward trend.

In all of the above patent documents, the history such as the weight value and the body composition value is merely displayed, and it is difficult for the user to grasp how to achieve the desired weight change (diet, weight maintenance, and the like).

In view of solving the above problems, it is an object of the present invention to provide a weight scale enabling the trend in weight change to be grasped even with the measurement of a relatively short period of time.

It is another object of the present invention to provide a weight scale for presenting a guideline for achieving the desired weight change so as to be easily understood by the user.

Means for Solving the Problems

To achieve the above object, the present invention performs measurement and display of weight through the following means or processes. In other words, a weight scale according to the present invention includes: weight measurement means; storage means for storing a weight measurement value along with measurement day and time; determination means for determining whether a fluctuation range of the weight measurement value in the same day is within a predetermined reference range; and display means for displaying a percentage of the days determined that a daily weight fluctuation is within the reference range in a predetermined period.

The weight of a human is known to be the least in the morning (or when waking up) and to increase at night (or before going to bed), compared to the morning, in one day. As the weight decreases with metabolism or the like during sleep, the weight is known to decrease if the difference in weight between morning and night is within a predetermined value. Therefore, maintaining the weight fluctuation in a day within the reference range is important in managing weight, and a user can recognize the achievement to use for health management.

The present invention focuses on the above aspects, where the fluctuation of the weight measurement value in the same day to be determined by the determination means is suitably the difference between the weight in the morning (or when waking up) and the weight at night (or before going to bed). The predetermined reference range is suitably about ±500 grams, but may be suitably a value corresponding to the weight of the user (e.g., ±0.7% of weight). As sudden loss of weight is not desirable in terms of health, a lower limit value is provided to the reference range.

The predetermined period may be an arbitrary period, but is suitably one week or an integer multiples thereof taking into consideration that a schedule of a person is repeated in units of one week in most cases.

The user can know the trend in weight change by recognizing a percentage (the percentage is hereinafter also simply referred to as "achievement ratio") of the day determined that the weight fluctuation in a day of the predetermined period is within the reference range. In other words, the weight demonstrates a downward trend the higher the percentage of achieving the reference. The trend in weight change is difficult to grasp due to variation by daily fluctuation if the daily weight is simply displayed, but the trend in weight change can be grasped if the achievement ratio of the day, in which the daily fluctuation range is within the reference, is known as in the present invention.

The display means in the present invention suitably displays the percentage of the day determined that the weight fluctuation of the day is within the reference range, and also displays the change in weight in the predetermined period. The display of change in weight in the predetermined period includes displaying the average value of the weight measured in the previous predetermined period (e.g., from present day to one week before), or displaying the average value of the weight measured in the predetermined period (e.g., from one week before to two weeks before) before the relevant predetermined period, or displaying the difference of these average values.

The user can easily understand the relationship of the achievement ratio and his/her weight change by displaying together the achievement ratio of the daily fluctuation management and the weight change in the period. As the weight change (decrease) becomes larger the higher the achievement ratio, the user can easily maintain the motivation to have the daily fluctuation within the reference range. The relationship of the achievement ratio and the weight change is not constant due to the lifestyle (e.g., amount of exercise), basal metabolism amount, and the like of the user. Thus, it is possible to grasp what extent of the weight change can be obtained with what extent of the achievement ratio.

The reference range may be automatically changed if the loss of weight is small although the achievement ratio is high or the loss of weight is large although the achievement ratio is low. A display urging to change the setting of the reference range may be made in such case. Thus, the value of an appropriate reference range can be used by changing the reference range according to the user.

Preferably, the display means according to the present invention also displays an average value of the daily weight fluctuation value in the predetermined period. Therefore, the user can understand his/her lifestyle habit (e.g., eating too much or the like) by displaying the average value of the daily fluctuation.

Preferably, the display means according to the present invention displays in a graph a daily weight fluctuation value in the predetermined period for every day. The graph to be displayed is suitably a bar graph, a line graph, or the like. The transition of the daily fluctuation value in each day of the period can thus be easily understood, and whether or not the lifestyle is irregular can be easily understood.

Preferably, the display means according to the present invention displays in animation the day-to-day daily weight fluctuation value in the predetermined period for every day. It is known that the lifestyle is more irregular the larger the variation of the daily fluctuation value being displayed in animation, and that the lifestyle habit is stable the smaller the variation.

The weight scale according to the present invention suitably diagnoses the health state based on the average value of the weight fluctuation value in a day and/or deviation from the reference value of the daily weight fluctuation value in the predetermined period. Health guideline advice is suitably made based on the diagnosis result. The health state is diagnosed by calculating the degree of lifestyle irregularity based on the average value or the standard deviation of the weight fluctuation value, the average of the amount greater than (or smaller than) the reference range of the fluctuation value, and the like. A warning display to reconsider the lifestyle habit is suitably made if the degree of lifestyle irregularity is greater than or equal to a predetermined threshold value.

Preferably, the weight scale according to the present invention further includes: body composition value measurement means for measuring a body composition value; wherein the display means performs a display to urge measurement by the body composition value measurement means when change in weight in the predetermined period is greater than a predetermined threshold value.

The present invention can be recognized as a weight scale including at least some of the above means. The present invention can also be recognized as a display method in the weight scale including at least some of the above processes, or a program for realizing such a method. Each of the means and processes described above can be combined as much as possible to configure the present invention.

Effect of the Invention

According to the present invention, a trend in weight change can be grasped even in measurement of a relatively short period.

DESCRIPTION OF THE REFERENCE SYMBOLS

Figure 1:
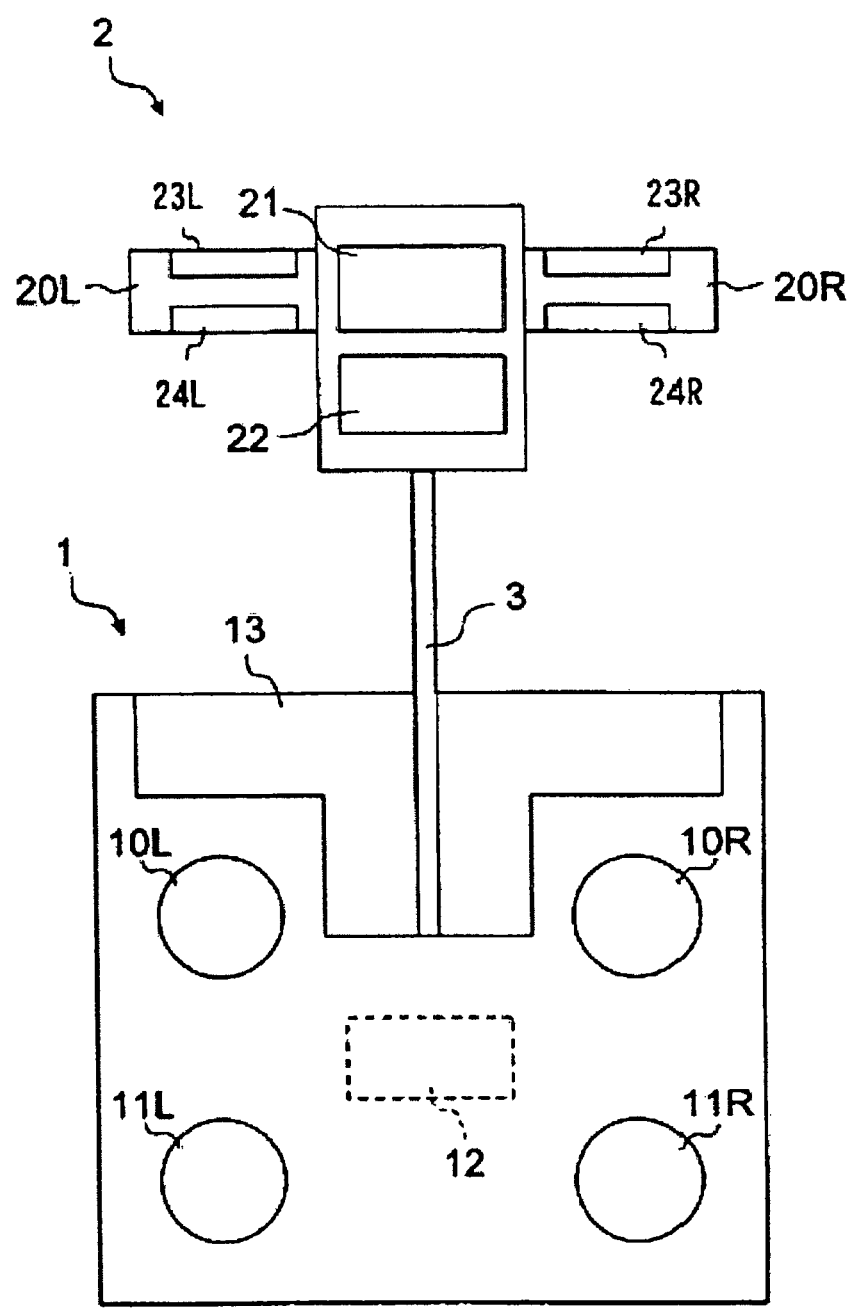
FIG. 1 is a view showing an outer appearance of a weight scale according to the present embodiment.

1 Main body
2 Holder
3 Cable
12 Weight measurement unit
21 Display unit
22 Operation unit
25 Control unit
27 Storage unit
28 Timer

BEST MODE FOR CARRYING OUT THE INVENTION

The preferred embodiment of the present invention will be specifically described below in an illustrative manner with reference to the drawings. The dimension, material, shape, relative arrangement, and the like of the configuring parts described in the present embodiment are not intended to limit the scope of the present invention unless a specific description is not particularly made.

(Configuration of Weight Scale)

FIG. 1 shows an outer appearance of a weight scale according to the present embodiment. The weight scale (body composition meter) capable of simultaneously measuring the body composition with the weight will be illustrated.

The weight scale is schematically configured by a main body 1 and a holder (display operation unit) 2. The main body 1 and the holder 2 are connected with a cable 3 to enable transmission and reception of signals. The main body 1 and holder 2 may be connected by wireless communication. When not in use, the holder 2 and the cable 3 are accommodated in a holder accommodating unit 13 of the main body 1.

Four foot electrodes 10L, 10R, 11L, 11R are arranged on an upper surface of the main body 1. The electrodes 10L, 10R are electrodes for applying a current to the back of left and right feet, and the electrodes 11L, 11R are electrodes for detecting a voltage from the back of the left and right feet. The main body 1 incorporates a weight measurement unit 12. The weight scale according to the present embodiment measures a daily fluctuation of the weight, where measurement accuracy is preferably 50 grams (or not more than 50 grams), but the measurement accuracy may be 100 grams.

The holder 2 includes left and right grips 20L, 20R, a display unit 21, an operation unit 22, and the like. The display unit 21 is a unit for displaying measurement results and guidance, as hereinafter described, and is configured by a liquid crystal display, and the like. The operation unit 22 includes a user interface for selecting a registration number (user), switching the display, and inputting other information. The display unit 21 and the operation unit 22 are also preferably configured with common hardware using a touch panel type display.

The grips 20L, 20R respectively includes an electrode 23L, 23R for applying a current to a palm of a hand, and an electrode 24L, 24R for detecting a voltage from the palm of the hand.

Figure 2:
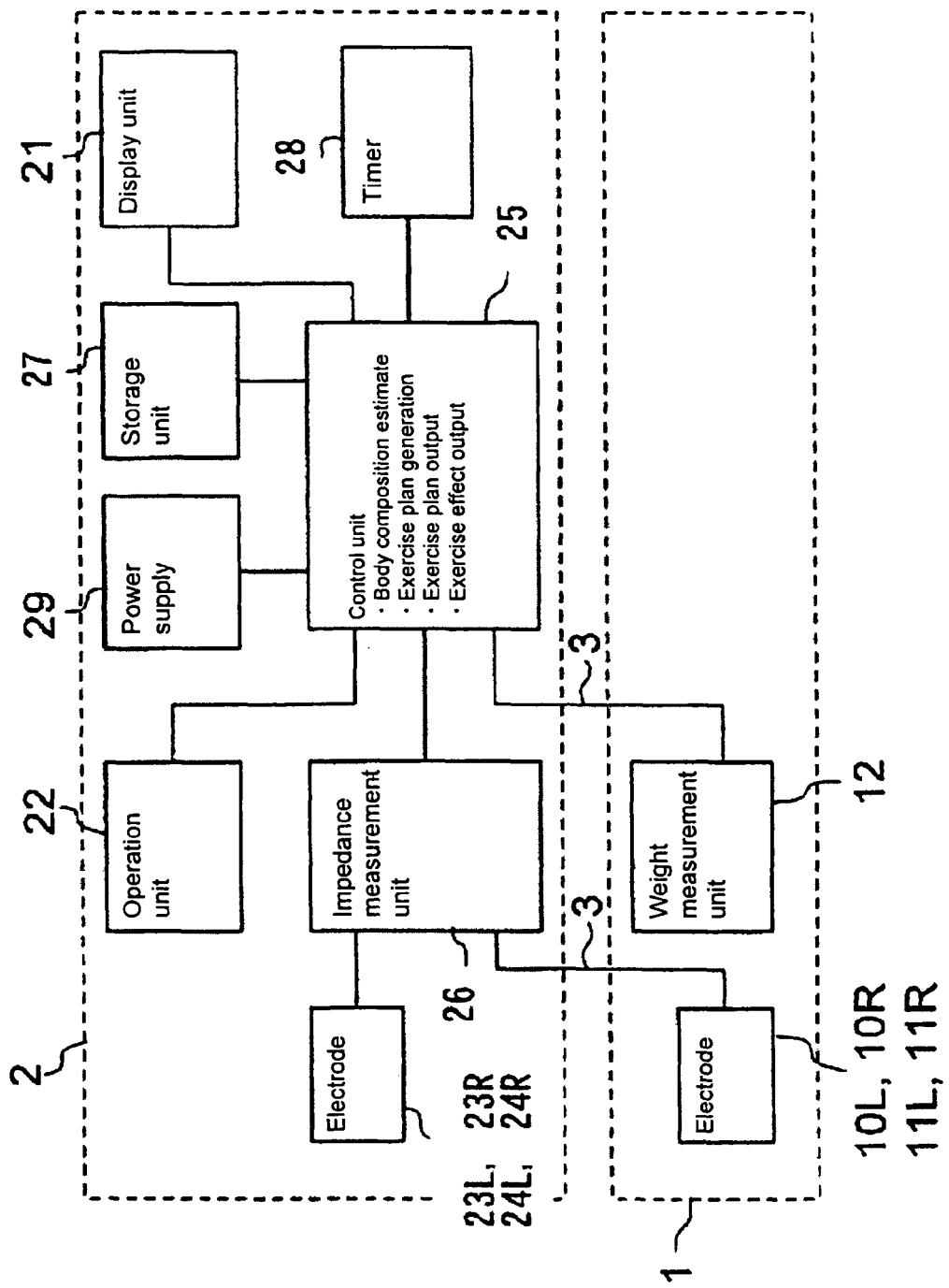
FIG. 2 is a block diagram showing a configuration of the weight scale according to the present embodiment.

FIG. 2 is a block diagram showing a configuration of the weight scale. As shown in FIG. 2, the holder 2 incorporates a control unit 25, an impedance measurement unit 26, a storage unit 27, a timer 28, a power supply 29, and the like.

The control unit 25 has a function of managing the measured weight value and the like with measurement day and time in the storage unit 27, a function of determining whether the daily fluctuation of the weight value is within a predetermined fluctuation range, a function of making a display of the achievement ratio of the daily fluctuation, and the like. The control unit 25 is configured by a CPU (calculation processing device), a memory, and the like, and the various functions above are realized when the CPU executes a program. Some of or all of the functions of the control unit 25 may be configured with a dedicated chip.

The impedance measurement unit 26 is means for measuring an in-vivo impedance by applying a predetermined current to a living body from the foot electrodes 10L, 10R and the hand electrodes 23L, 23R and detecting the voltage with the foot electrodes 11L, 11R and the hand electrodes 24L, 24R according to the control of the control unit 25.

The storage unit 27 is configured by a storage medium such as a non-volatile memory. The storage unit 27 stores the measurement results (measurement values) of the weight and the body composition, etc. by users (by registration numbers) in time-series. The storage unit 27 also stores attribute data (sex, age, height) of each user. The storage unit 27 further stores the reference range of the daily fluctuation value of the weight value. The reference range is ±500 grams.

In the weight scale of the present embodiment, a plurality of (e.g., four) users can be registered, and the user can be selected by specifying the registration number with the operation unit 22.

In the present embodiment, various types of electrodes and the impedance measurement unit are arranged to enable the measurement of the body composition, but the weight scale may be configured to measure only the weight value.

(Weight Measurement Function)

A flow of a standard process of when measuring the weight will be described along a flowchart of FIG. 3.

When the user turns ON the power supply of the weight scale, the control unit 25 executes a correction process of the weight scale (S10). When the user gets on the main body 1 and comes to rest in a measurement posture after the correction process is completed, the weight is measured by the weight measurement unit 12 (S11).

The measured weight is stored in the storage unit 27 with date and time information obtained from the timer 28 (S12). Here, the weight measured from 4 o'clock to 10 o'clock is stored as the weight of "morning", and the weight measured from 18 o'clock to 24 o'clock is stored as the weight of "night". This time band is preferably set for every user. The measurement may be performed after the user specifies which time band the weight is through the operation unit 22.

Figure 4:
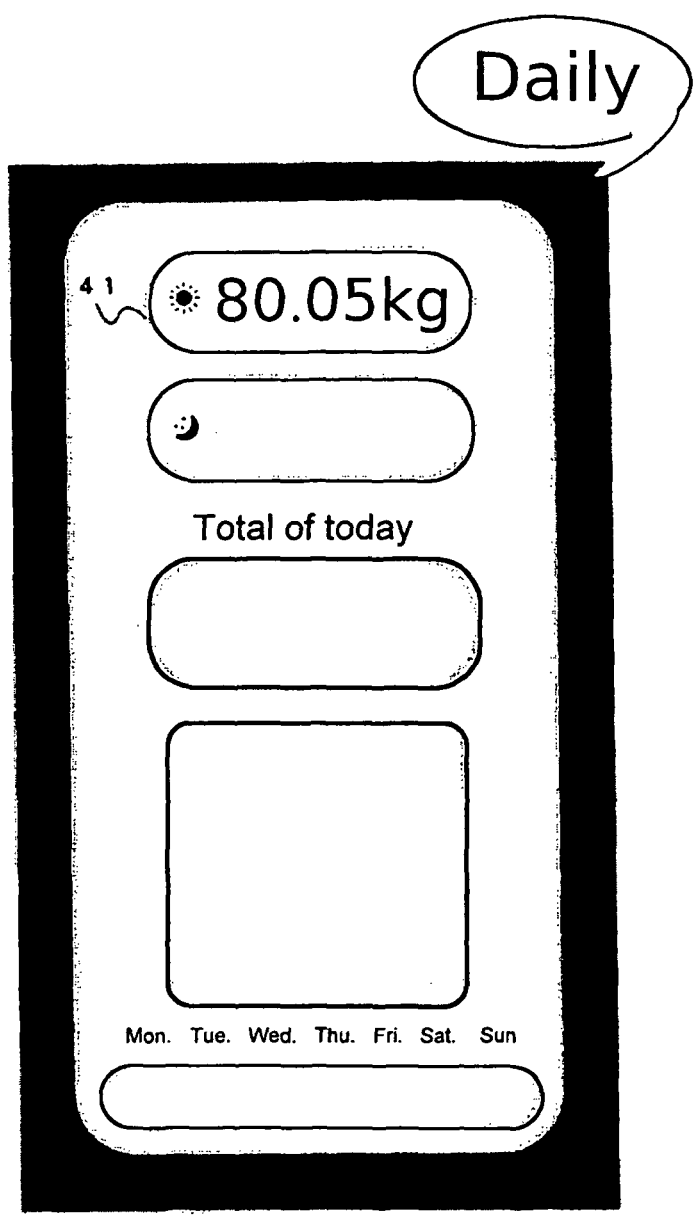
FIG. 4 is a view showing an example of a display screen after morning measurement.
Figure 5:
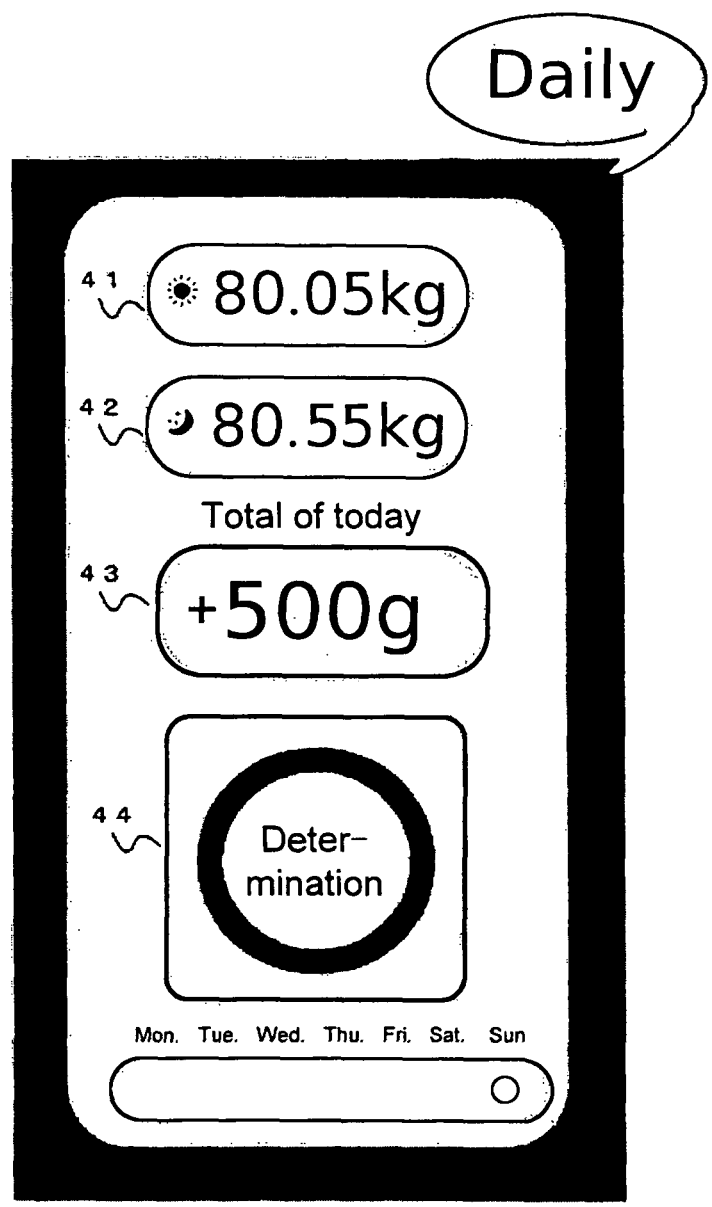
FIG. 5 is a view showing an example of a display screen after night measurement.

The measured weight is displayed on the display unit 21 (S13). An example of a display screen of the measurement result displayed on the display unit 21 will be described using FIGS. 4 and 5. After the morning measurement, the measurement value is displayed in a morning measurement value 41, as shown in FIG. 4. In this case, "80.05 kg" is displayed as a morning measurement value 41. After the night measurement, the morning measurement value 41, a night measurement value 42, a daily fluctuation amount (increased amount of one day) 43, and a determination result 44 are displayed, as shown in FIG. 5. Since "80.55 kg" is measured as the night measurement value 42, 500 g, calculated from (night measurement value)−(morning measurement value), is displayed in the daily fluctuation amount 43. In the determination result 44, the determination result of whether or not the daily fluctuation amount is within the reference range stored in the storage unit 27 is displayed. The reference range is 500 g and the daily fluctuation amount is also 500 g, and thus a display (◯ display) indicating that the reference is satisfied is made in the determination result 44. If the reference is not satisfied, a display (x display) indicating the same is made. The determination result for this day is added to a determination result history 45 displaying the determination result for the past one week. The determination result history 45 displays the determination result for the past one week with the right end as the measurement day (present day). In FIG. 5, the display for only the measurement days is made since the previous data are not accumulated.

The analyzing process for analyzing the measurement result for the previous one week (corresponding to predetermined period) is then executed (S14). In the analyzing process, calculation and display of the percentage of the days the daily fluctuation is within the reference range, the weight fluctuation during the period, and the like are performed for the previous one week. After the display of the analysis result is finished, the power supply is turned OFF (S15), and the process of the weight scale is terminated.

(Analyzing Process)

Figure 6:
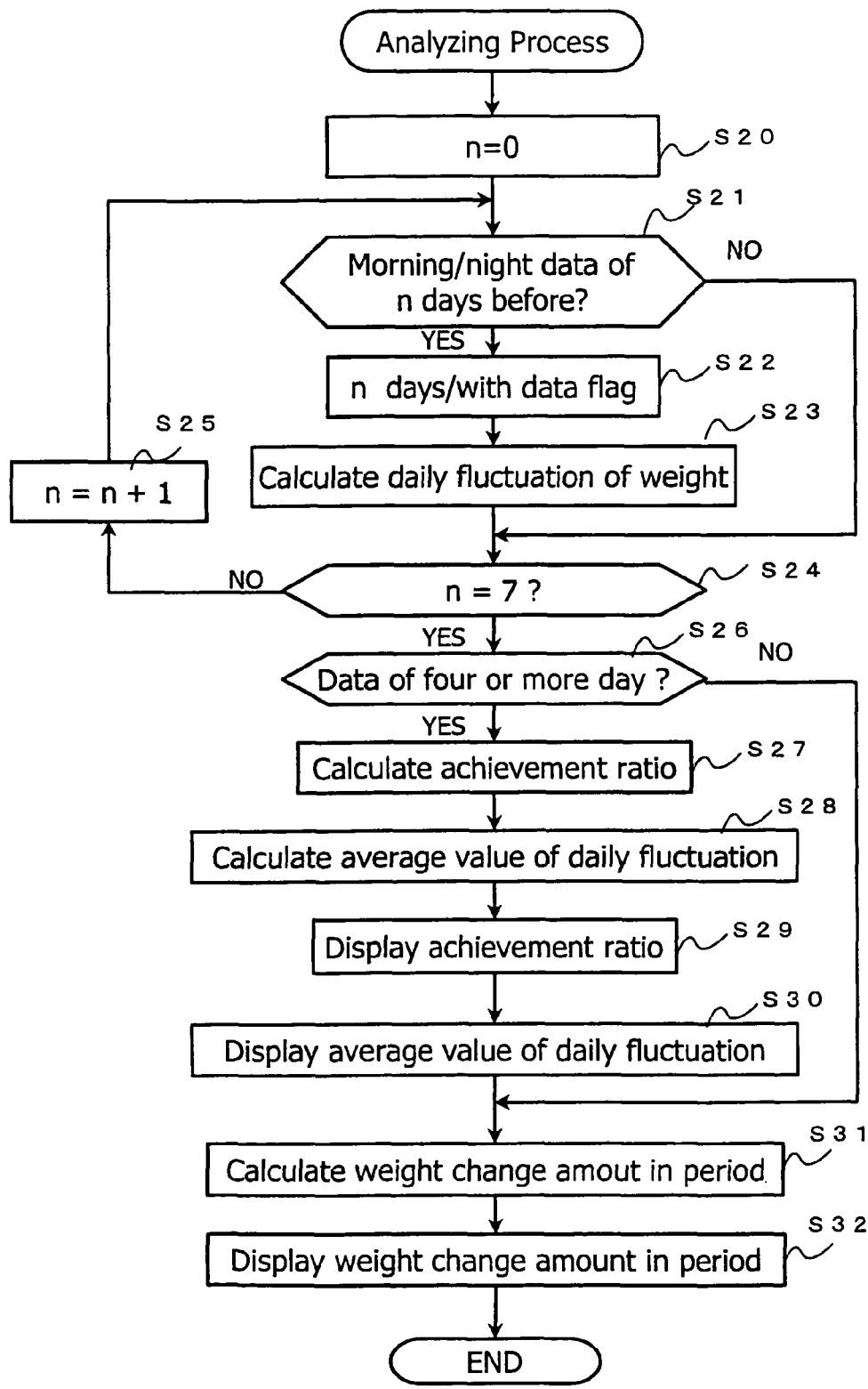
FIG. 6 is a flowchart showing a flow of analysis and display process of a daily fluctuation.

The details of the analyzing process of S14 will be described along a flowchart of FIG. 6.

When the analyzing process starts, the difference between the weight value measured in the morning and the weight value measured at night is calculated for the previous one week. Specifically, a counter n is first initialized to zero (S20), and whether or not both the morning measurement value and the night measurement value of n days before exist in the storage unit 27 is determined (S21). If they exist (S21: YES), a flag of n days before is set to "with" (S22), and the difference between the measurement values of morning and night is calculated (S23). If the data n days before do not exist (S21: NO), the flag n days before is remained "without", and the process of calculating the difference between the measurement values of morning and night is skipped. Then, whether or not the process is performed for one week (seven days) is determined (S24), where n is incremented if one week is not reached (S25), and the processes from S21 are repeated.

After the data for one week is finished examining (S24: YES), whether or not the days the data of morning and night exist are four days or more is determined (S26). If four days or more (S26: YES), the percentage (achievement ratio) of the days the daily fluctuation is within the reference range is calculated (S27). The achievement ratio is calculated as (number of days daily fluctuation is within reference range) ÷ (number of days measurement data are present). The average value of the daily fluctuation is calculated for one week (S28).

Figure 7:
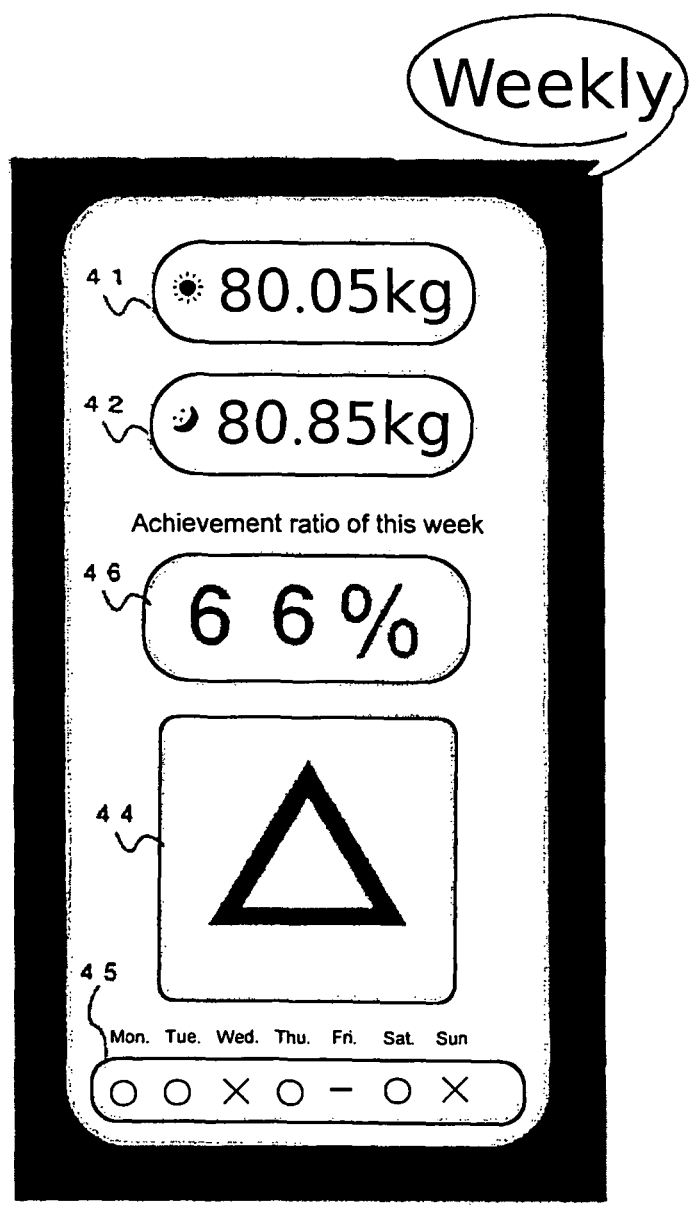
FIG. 7 is a view showing an example of a display screen displaying an achievement ratio.

The achievement ratio calculated in S27 is displayed on the display unit 21 (S29). FIG. 7 is an example of the display screen for displaying the achievement ratio. The determination result history 45 indicating if the daily fluctuation is within the reference range is displayed for the past one week at the lower part of the display unit 21. The day where the daily fluctuation is within the reference range is displayed with "○", and the day where the daily fluctuation is not within the reference range is displayed with "x". Furthermore, "-" is displayed for the day measurement is not made. In the achievement ratio 46, the achievement ratio calculated in S27 is displayed. In this case, "number of days daily fluctuation is within reference range" is four days, and "number of days measurement data are present" is six days, and thus 66% is displayed for the achievement ratio. Furthermore, "○", "Δ", "x", and the like are displayed according to the achievement ratio in the determination result 44. The relevance of the achievement ratio and the evaluation may be appropriately set.

Figure 8:
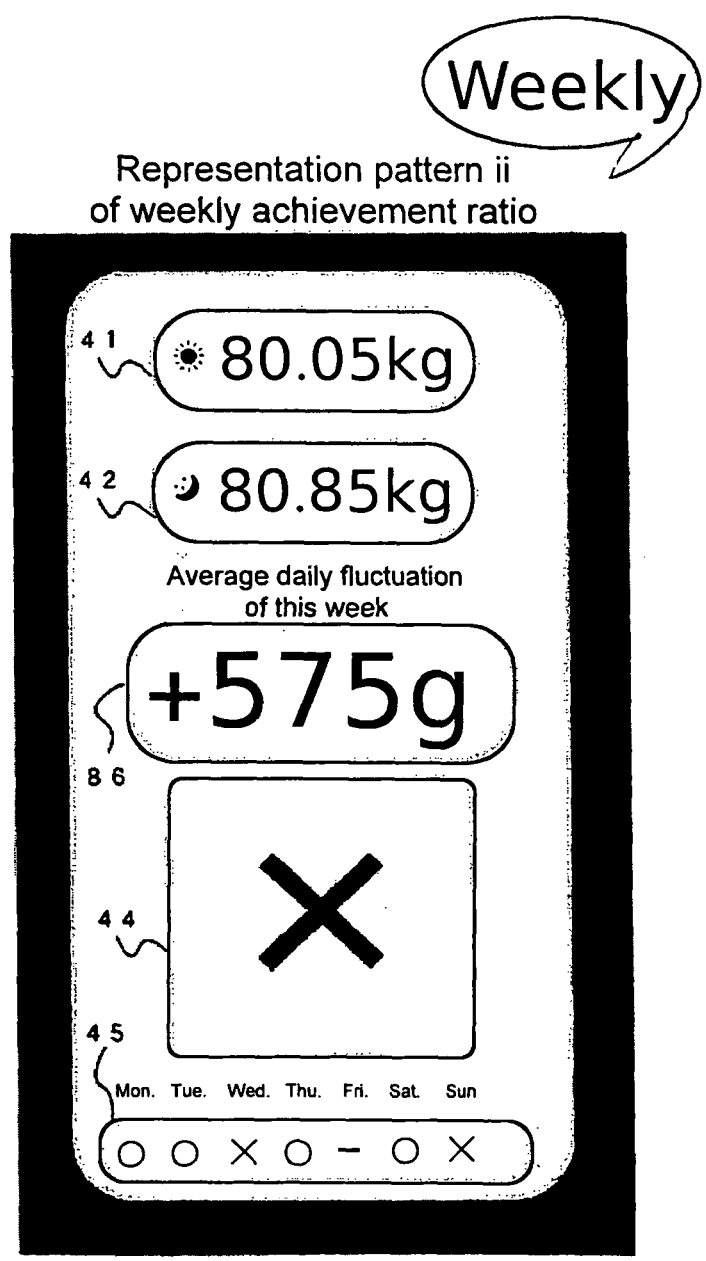
FIG. 8 is a view showing an example of a display screen displaying an average value of the daily fluctuation.

The average value of the daily fluctuation amount calculated in step S28 is then displayed (S30). A transition of the screen display from S29 to S30 may be an automatic transition after elapse of a predetermined time, or the user may instruct the switching of the display screen. FIG. 8 is an example of a display screen displaying the average value of the daily fluctuation amount. As shown in FIG. 8, the average value of the daily fluctuation amount calculated in S28 is displayed in the average daily fluctuation 86. In the determination result 44, the determination result corresponding to whether or not the average value of the daily fluctuation is within the reference range is displayed. For instance, as shown in FIG. 8, if the average value of the daily fluctuation is +575 grams, "x" is displayed for the determination result. If the average value of the daily fluctuation is ±500 grams, "○" is displayed for the determination result.

In FIGS. 7 and 8, the measurements of morning and night on the day of the measurement day are displayed in the morning measurement value 41 and the night measurement value 42, but such a display may be erased when displaying the achievement ratio and the like for one week.

If the measurement days within the past week are three days or less (S26: NO), the display of the achievement ratio and the like of one week does not provide a great meaning, and thus the processes of S27 to S30 are skipped. In this case, "measurement of four or more days per week is necessary for weekly analysis" and the like may be displayed to urge the user to measure weight.

For how many days in one week to request for the measurement data as a determination reference in S26 may be appropriately designed. For instance, it may be five or more days, or may be three or more days. The display of S27 to S30 may be constantly performed irrespective of the number of measurement days.

Figure 9:
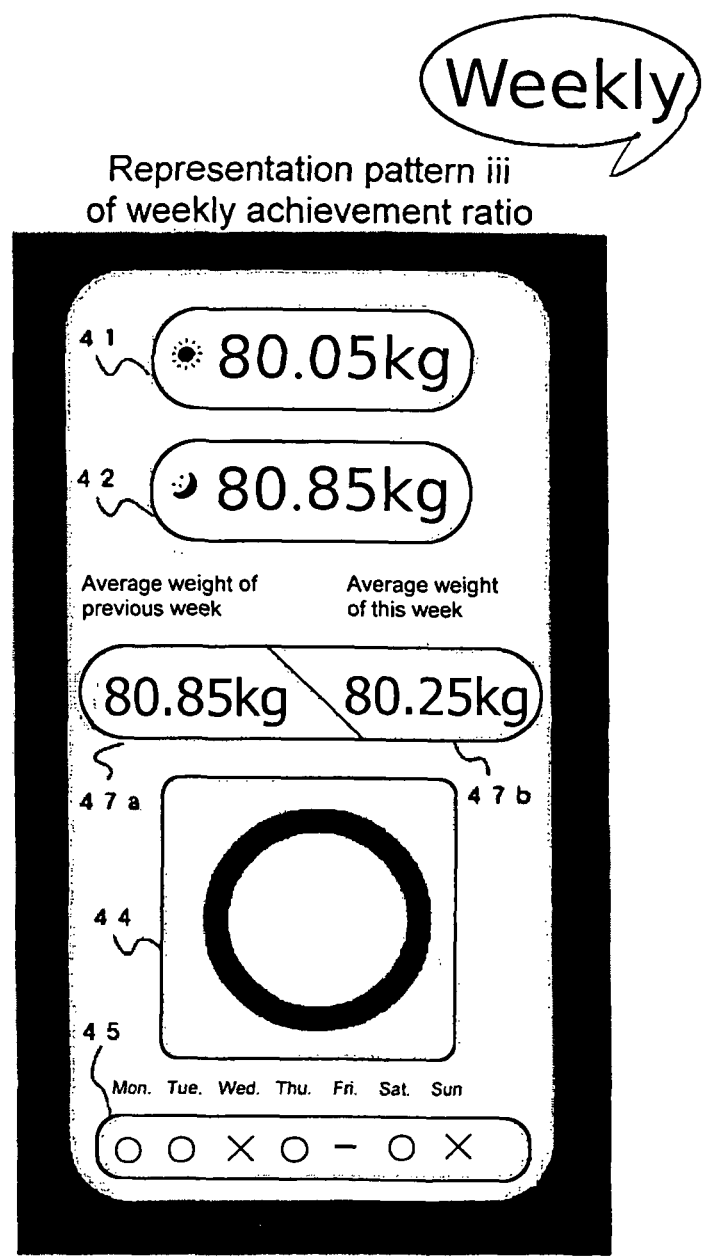
FIG. 9 is a view showing an example of a display screen displaying a change in weight in a measurement period.

The change in weight in one week is then calculated (S31) and displayed (S32). For the change in weight, the difference between the average value of the weight value in the morning for one week for this week (from present day to six days before) and the average value of the weight value in the morning for one week for the previous week (from one week before to six days before that) is calculated. The influence by variation by days can be reduced by obtaining the difference in the average values within the measurement value. FIG. 9 is an example of a display screen displaying the change in average weight. In FIG. 9, an average weight 47a for the previous week and an average weight 47b for this week are displayed. "○" is displayed in the determination result 44 if the average of this week is smaller than the previous week, and "x" is displayed if greater. Only the difference in the average values may be displayed instead of displaying the respective average weight of the previous week and this week.

The display order of the display screen may be appropriately interchanged. A plurality of above items may be collectively displayed in one screen.

(Operation/Effects of Embodiment)

According to the weight scale of the present embodiment, the user can be made conscious to have the day-to-day daily fluctuation within the predetermined fluctuation range. Whether his/her weight demonstrates an upward trend or a downward trend can be grasped from the day-to-day daily fluctuation amount. In other words, the weight demonstrates a downward trend the greater the percentage of days the daily fluctuation is within the reference range, and the smaller the average of the daily fluctuation amount. In this case, the trend in change of his/her weight can be recognized from the measurement data of a significantly short period compared to when the measurement is simply performed once a day and the trend in change of weight is recognized from the history thereof.

(Variant)

Various variants can be assumed for the display of day-to-day weight value and the display of weekly analysis result.

First Variant

For instance, the display of the day-to-day weight value may be a display simultaneously using a graph as shown in FIG. 10 instead of a display of only numerical values as shown in FIGS. 4 and 5. As shown in FIG. 10, the measurement weight is not only displayed as a numerical value in the morning measurement value 41 and the night measurement value 42 in the display unit 21, but a graph display is made in an increasing/decreasing graph 48. The increasing/decreasing graph 48 displays the fluctuation from the morning weight value, where the background is shown in green if within an appropriate range 49 (plus/minus 500 grams), and the background is shown in red if outside the appropriate range (excessively increased 50, excessively decreased 51) so as to be easily understood visually in which range satisfactory result is obtained.

Figure 10A:
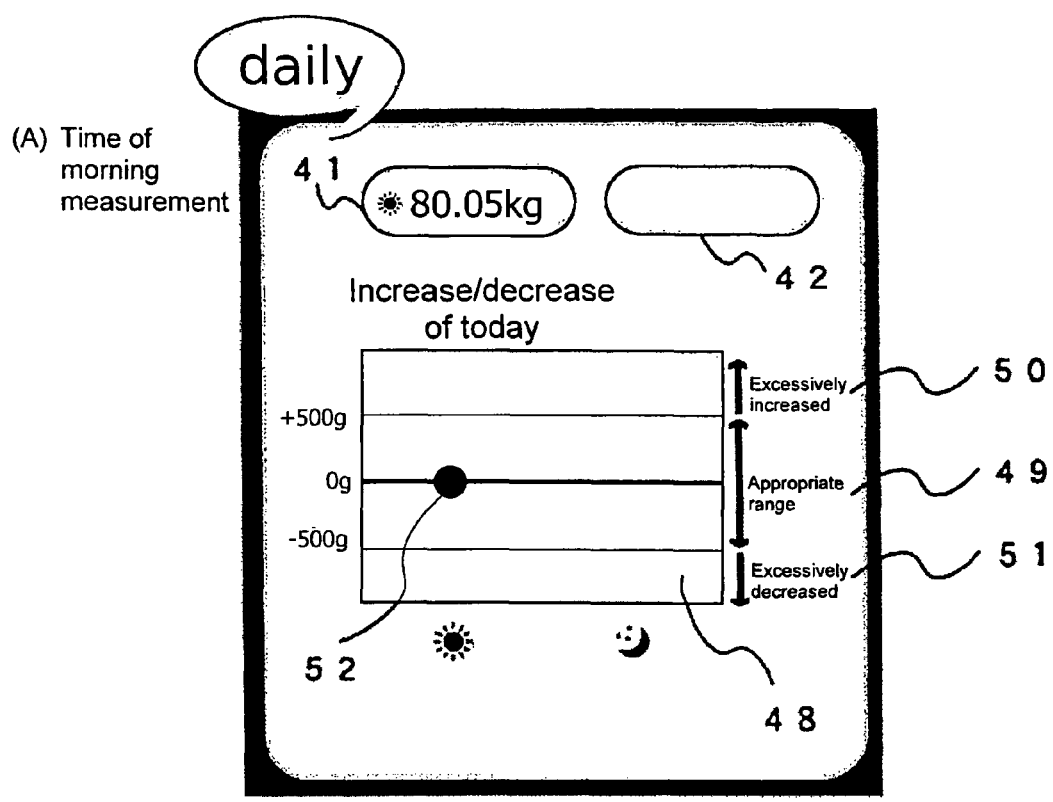
FIG. 10A is a view showing another example of a display screen (time of morning measurement) displaying the daily fluctuation.
Figure 10B:
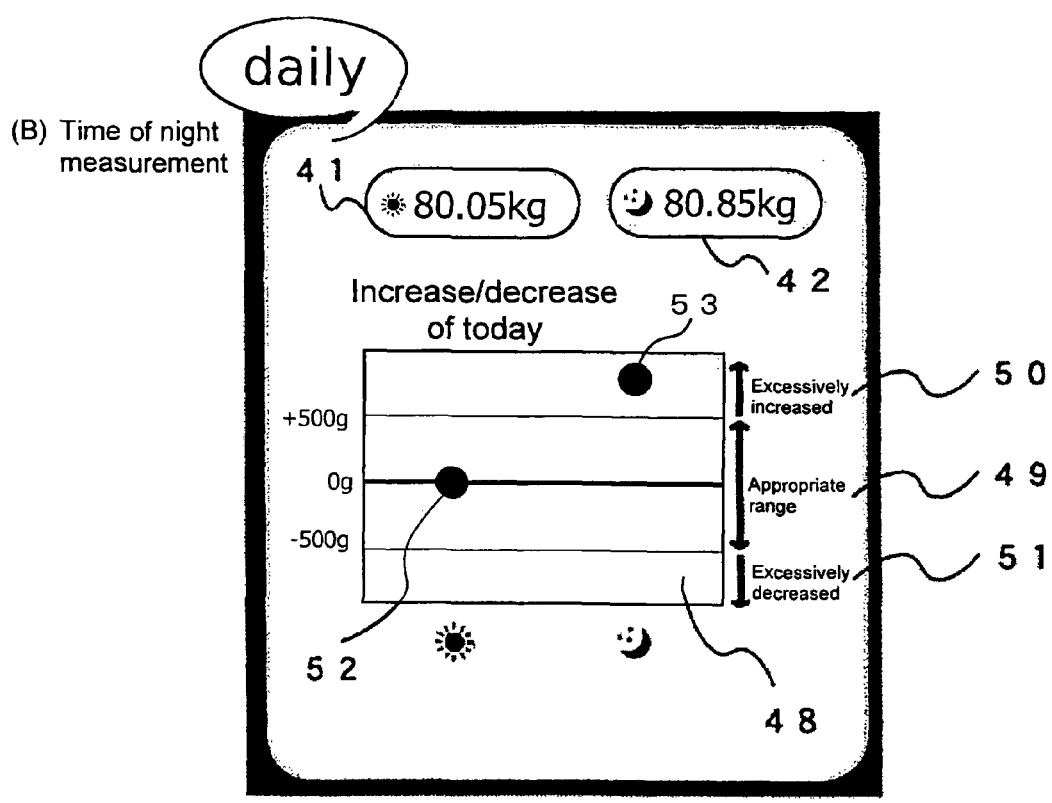
FIG. 10B is a view showing another example of a display screen (time of night measurement) displaying the daily fluctuation.

If the weight is measured in the morning, the measurement value is displayed in the morning measurement value 41, and a mark indicating that the weight is measured in the morning is given in the increasing/decreasing graph 48, as shown in FIG. 10A. Specifically, a circle 52 is displayed on an increasing/decreasing reference line. If the weight is measured at night, the measurement value is displayed in the night measurement value 42 and a mark is given to a position corresponding to the fluctuation from the morning measurement value in the increasing/decreasing graph 48, as shown in FIG. 10B. In FIG. 10B, the night measurement value is increased by 800 grams compared to the morning, and thus a circle 53 is displayed in the "excessively increased" region 50.

In this manner, the fluctuation range can be easily understood visually by displaying the day-to-day fluctuation in a graph.

Second Variant

Figure 11:
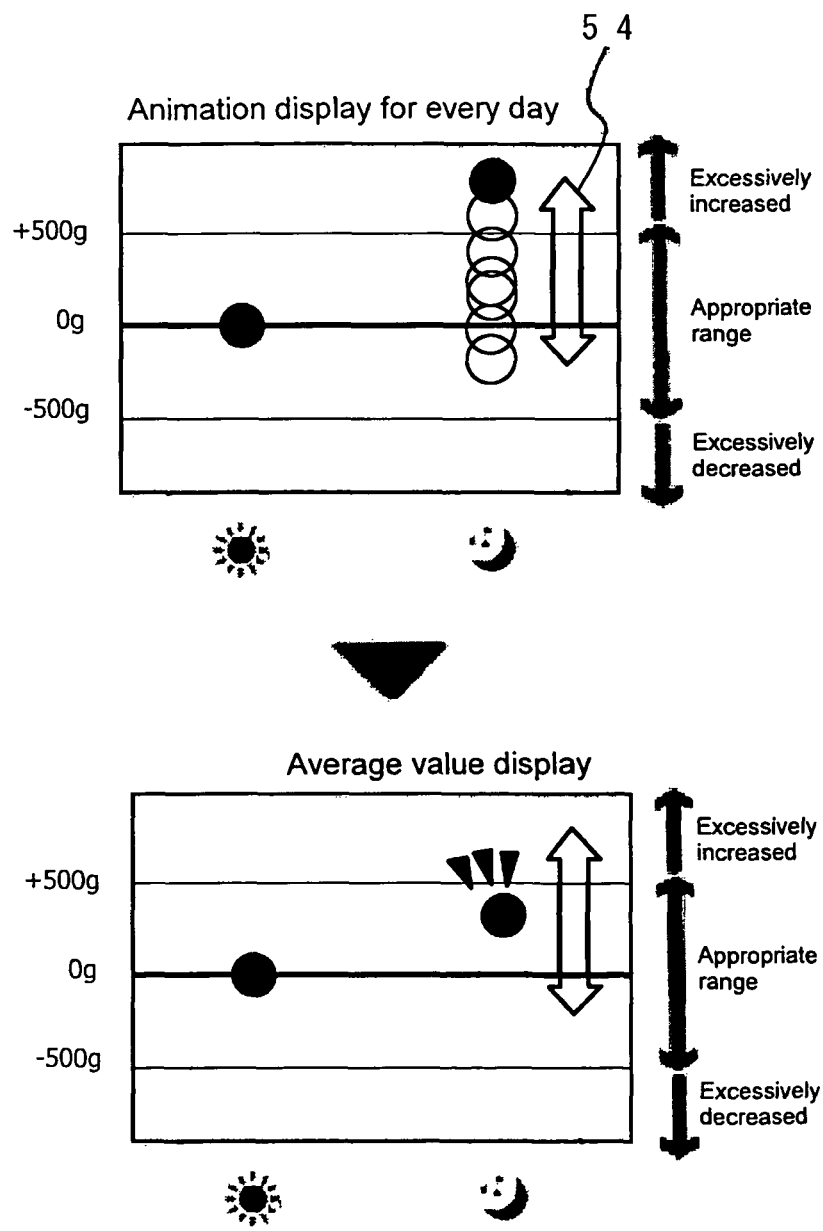
FIG. 11 is a view showing an example of a display screen displaying the daily fluctuation in animation.

The graph display of the first variant can also be used in the display of the weekly analysis result. A display example using the graph display in the display of the average value of the daily fluctuation in S28 of the flowchart of FIG. 3 is shown in FIG. 11.

In this case, the fluctuation amount in the respective day in the measurement period (one week) is displayed in animation before displaying the average value of the daily fluctuation. Specifically, the fluctuation amount for one week is displayed in a frame-by-frame advance, as shown in FIG. 11. The average value of the fluctuation is displayed after all the fluctuations for one week are displayed.

It can be understood that the lifestyle is irregular if the varying range 54 for every day is large, and it can be understood that the lifestyle is stable if the varying range 54 is small by animation-displaying the fluctuation amount for every day.

Third Variant

Figure 12:
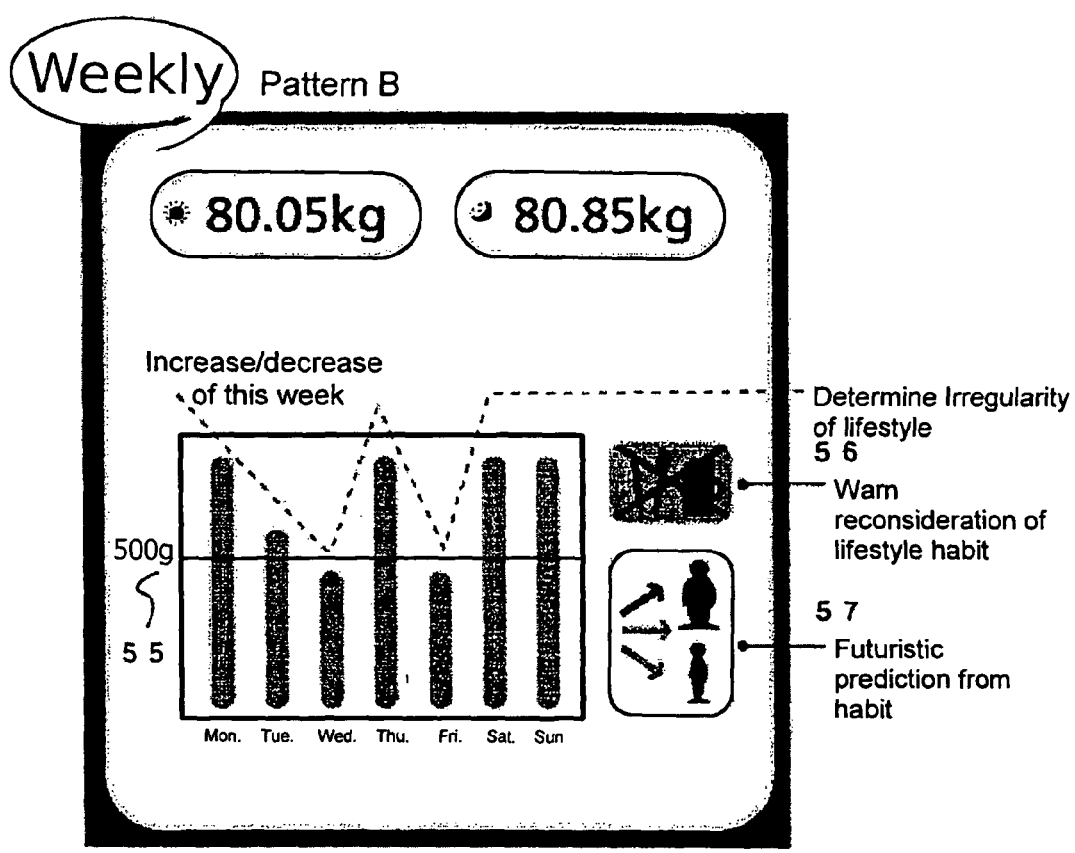
FIG. 12 is a view showing an example of a display screen displaying the daily fluctuation in a graph.

Furthermore, the daily fluctuation amount of every day may be displayed in a bar graph, as shown in FIG. 12. It may also be displayed in a line graph. The user can easily understand his/her health condition by also displaying a reference line 55 indicating the reference range in the relevant graph.

Fourth Variant

In all the examples described above, the history of the daily fluctuation and the achievement ratio are merely displayed, but suitably, a health guideline advice can be given using such analysis results. For instance, the irregularity of the lifestyle can be calculated from the daily fluctuation of every day, and a display urging to reconsider the lifestyle habit is preferably made (warning 56 of FIG. 12, and the like) when determined that the irregularity of the lifestyle is large. The degree of lifestyle irregularity is suitably calculated based on the average value and the variance value of the daily fluctuation amount. That is, the degree of irregularity is determined as large if the average value is large compared to the reference value. The degree of lifestyle irregularity is also determined as large if the daily fluctuation amount greatly differs depending on the days (if variance is large) although the average value is within the reference range.

Specifically, assuming the daily fluctuation value of each day of the week is $\Delta W\text{mon}, \Delta W\text{tue}, \Delta W\text{sun}$, and the fluctuation amount of an arbitrary day of the week between Tuesday and Sunday is $\Delta WN$. In this case, the average value $\Delta WM$ of the daily fluctuation amount from Monday to the arbitrary day of the week is expressed as, $$\Delta WM = (\Delta W\text{mon} + \Delta W\text{tue} + \ldots + \Delta WN)/N$$

In this case, the degree of lifestyle irregularity is determined as large when $$\Delta WM \geq \Delta WC1 \qquad (1)$$

600 grams can be used as an example of $\Delta WC1$.

Assuming the standard deviation of the daily fluctuation from Monday to the arbitrary day of the week is $\Delta WSD$, the degree of lifestyle irregularity is determined as large even if $\Delta WM \Delta WC1$ is satisfied if $$\Delta WSD \geq \Delta WC2 \qquad (2)$$

300 grams can be used as an example of $\Delta WC2$.

Therefore, determination is made that the degree of lifestyle irregularity is not large if both conditions (1), (2) are not met. There may be adopted a configuration of, without calculating the degree of lifestyle irregularity using both the average value and the standard deviation, determining the degree of lifestyle irregularity based only on either one.

The prediction of the future weight change may be suitably displayed from the analysis result of the daily fluctuation (prediction display 57 of FIG. 12, and the like).

Figure 3:
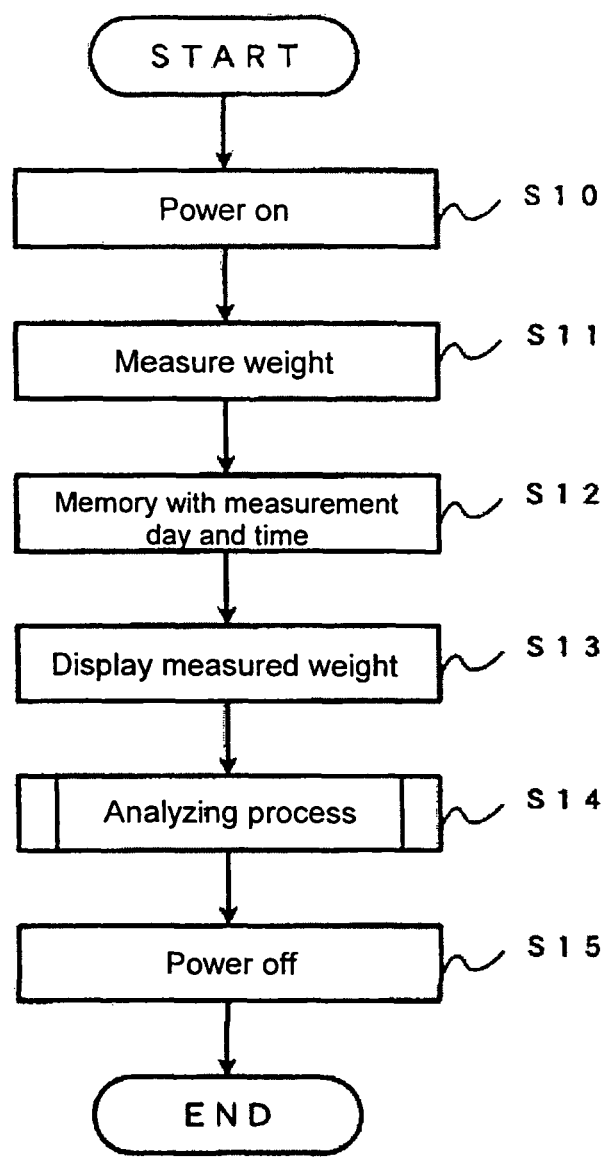
FIG. 3 is a flowchart showing a flow of a weight measurement process.

In S31, S32 of the flowchart of FIG. 3, if the weight change in one week is greater than a predetermined threshold value (excessively increasing, excessively decreasing), a display urging to measure the body composition may be suitably made.

Fifth Variant

In the above described description, description has been made with the reference range of the daily fluctuation as ±500 grams. However, the reference range may suitably be a value corresponding to the weight value (±0.7% and the like of weight). The user thus can perform a more suited analysis corresponding to the physical attribute. The reference range may have a range of between +N grams to −M grams (N, M>0, N≠M) and not only a range in which the amount of increase and the amount of decrease are equal as in ±N grams.

The reference range is selected such that the weight demonstrates a downward trend if the daily fluctuation in the measurement period is within the reference range, but whether the weight decreases if the daily fluctuation is actually within the reference range varies between individuals. The control unit 25 thus can compare the achievement ratio and the weight change (change in week) to automatically change the reference range or make a display urging the user to make setting changes. For instance, if the weight does not decrease although the achievement ratio is high, a change is made to reduce the reference range. If the weight does not increase (or decrease) although the achievement ratio is low, a change is made to increase the reference range.

In this manner, the reference range is adjusted to an appropriate value according to each user.

The invention claimed is:

1. A weight scale comprising:
   a weight measurement unit;
   a storage unit configured to store a weight measurement value along with a measurement day and time;
   a determination unit configured to determine whether a fluctuation range of the weight measurement value in a same day is within a predetermined reference range;
   an analyzing unit configured to determine a percentage of the days that a daily weight fluctuation is within the reference range in a predetermined period; and
   a display unit configured to display the percentage of the days that the daily weight fluctuation is within the reference range in the predetermined period;
   wherein the weight scale is configured to change the reference range or to generate an indicator to change the reference range based on the percentage of the days that the daily weight fluctuation is within the reference range in the predetermined period and a weight change in the predetermined period.

2. The weight scale according to claim 1, wherein the display unit is further configured to display an average value of the daily weight fluctuation value in the predetermined period.

3. The weight scale according to claim 1, wherein the display unit is further configured to display, in a graph, a day-to-day daily weight fluctuation value in the predetermined period.

4. The weight scale according to claim 1, wherein the display unit is further configured to display, in animation, the day-to-day daily weight fluctuation value in the predetermined period for every day.

5. The weight scale according to claim 1, being configured to diagnose a health state based on at least one of an average value of the daily weight fluctuation value and a deviation from the reference range of the daily fluctuation value in the predetermined period, and give a health guideline advice based on a diagnosis result.

6. The weight scale according to claim 1, further comprising:
   a body composition value measurement unit configured to measure a body composition value; wherein
   the display unit is further configured to indicate a measurement by the body composition value measurement unit when change in weight in the predetermined period is greater than a predetermined threshold value.

7. The weight scale according to claim 1, wherein the display unit is further configured to display a first average of weight measurement values in the predetermined period and a second average of weight measurement values in a period previous to the predetermined period or a difference between the first average and the second average.

* * * * *